(12) United States Patent
Greenwald et al.

(10) Patent No.: US 8,608,656 B2
(45) Date of Patent: Dec. 17, 2013

(54) SYSTEM AND METHOD FOR INTEGRATING CLINICAL INFORMATION TO PROVIDE REAL-TIME ALERTS FOR IMPROVING PATIENT OUTCOMES

(75) Inventors: Scott D. Greenwald, Medfield, MA (US); Nassib G. Chamoun, Needham, MA (US); Jeffrey C. Sigl, Medway, MA (US)

(73) Assignee: Covidien LP, Mansfield, MA (US)

( * ) Notice: Subject to any disclaimer, the term of this patent is extended or adjusted under 35 U.S.C. 154(b) by 467 days.

(21) Appl. No.: 12/752,288

(22) Filed: Apr. 1, 2010

(65) Prior Publication Data

US 2010/0256463 A1 Oct. 7, 2010

Related U.S. Application Data

(60) Provisional application No. 61/165,672, filed on Apr. 1, 2009.

(51) Int. Cl.
*A61B 5/00* (2006.01)

(52) U.S. Cl.
USPC .............. 600/301; 600/300; 707/706

(58) Field of Classification Search
USPC ............... 600/485, 508, 300–301; 705/2–5; 707/706
See application file for complete search history.

(56) References Cited

U.S. PATENT DOCUMENTS

| | | | |
|---|---|---|---|
| 4,869,253 A | 9/1989 | Craig, Jr. et al. | |
| 5,692,501 A * | 12/1997 | Minturn | 600/301 |
| 6,625,485 B2 * | 9/2003 | Levendowski et al. | 600/544 |
| 6,748,252 B2 | 6/2004 | Lynn et al. | |
| 6,839,581 B1 | 1/2005 | El-Solh et al. | |
| 7,181,264 B2 | 2/2007 | Wiesmann et al. | |
| 7,309,314 B2 | 12/2007 | Grant et al. | |
| 7,572,230 B2 | 8/2009 | Neumann et al. | |
| 7,668,579 B2 | 2/2010 | Lynn | |
| 7,706,852 B2 | 4/2010 | Baker, Jr. | |
| 7,758,503 B2 | 7/2010 | Lynn et al. | |
| 7,761,128 B2 | 7/2010 | Al-Ali et al. | |
| 7,853,456 B2 * | 12/2010 | Soto et al. | 705/2 |
| 2002/0038227 A1 * | 3/2002 | Fey et al. | 705/3 |
| 2002/0190863 A1 | 12/2002 | Lynn | |
| 2003/0004423 A1 | 1/2003 | Lavie et al. | |
| 2003/0092975 A1 * | 5/2003 | Casscells et al. | 600/300 |
| 2003/0158466 A1 | 8/2003 | Lynn et al. | |

(Continued)

FOREIGN PATENT DOCUMENTS

| | | |
|---|---|---|
| WO | WO-8801149 A1 | 2/1988 |
| WO | WO-2007067927 A2 | 6/2007 |
| WO | WO-2010002374 A1 | 1/2010 |

OTHER PUBLICATIONS

Mancini, E., et al., "Short Term Variability of Oxygen Saturation During Hemodialysis Is a Warning Parameter for Hypotension Appearance," Computers in Cardiology 2008; 35:881-883.

(Continued)

*Primary Examiner* — Bill Thomson
*Assistant Examiner* — Bobby Soriano

(57) ABSTRACT

Systems and methods for assessing a patient's risk of poor outcome in real-time are provided. The real-time risk may be used by a physician to guide decision making during a procedure.

23 Claims, 8 Drawing Sheets

(56) References Cited

U.S. PATENT DOCUMENTS

| | | |
|---|---|---|
| 2003/0187688 A1* | 10/2003 | Fey et al. .................... 705/2 |
| 2004/0034288 A1* | 2/2004 | Hennessy et al. ............ 600/300 |
| 2004/0116814 A1 | 6/2004 | Stranc et al. |
| 2004/0162499 A1 | 8/2004 | Nagai et al. |
| 2005/0062609 A9 | 3/2005 | Lynn |
| 2005/0119534 A1* | 6/2005 | Trost et al. ................... 600/300 |
| 2005/0144042 A1* | 6/2005 | Joffe et al. .................... 705/2 |
| 2005/0159656 A1* | 7/2005 | Hockersmith et al. ....... 600/315 |
| 2005/0203773 A1* | 9/2005 | Soto et al. ..................... 705/2 |
| 2005/0240091 A1 | 10/2005 | Lynn |
| 2005/0262031 A1* | 11/2005 | Saidi et al. .................... 706/21 |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0173257 A1 | 8/2006 | Nagai et al. |
| 2006/0189880 A1 | 8/2006 | Lynn et al. |
| 2006/0217603 A1 | 9/2006 | Nagai et al. |
| 2006/0235324 A1 | 10/2006 | Lynn |
| 2006/0266356 A1 | 11/2006 | Sotos et al. |
| 2006/0276695 A9 | 12/2006 | Lynn et al. |
| 2006/0281983 A1 | 12/2006 | Al-Ali et al. |
| 2006/0293922 A1* | 12/2006 | Seare et al. ................... 705/2 |
| 2007/0032733 A1* | 2/2007 | Burton .......................... 600/509 |
| 2007/0093721 A1 | 4/2007 | Lynn et al. |
| 2007/0129647 A1 | 6/2007 | Lynn |
| 2007/0136093 A1* | 6/2007 | Rankin et al. ................. 705/2 |
| 2007/0149860 A1 | 6/2007 | Lynn et al. |
| 2007/0191688 A1 | 8/2007 | Lynn |
| 2007/0191697 A1 | 8/2007 | Lynn et al. |
| 2008/0009684 A1* | 1/2008 | Corsetti et al. ............... 600/300 |
| 2008/0033254 A1* | 2/2008 | Kamath et al. ............... 600/300 |
| 2008/0061961 A1* | 3/2008 | John ........................ 340/539.12 |
| 2008/0147438 A1* | 6/2008 | Kil .................................. 705/2 |
| 2008/0162182 A1* | 7/2008 | Cazares et al. ................ 705/2 |
| 2008/0162352 A1* | 7/2008 | Gizewski ...................... 705/50 |
| 2008/0183499 A1* | 7/2008 | Tarkka et al. .................. 705/3 |
| 2009/0089079 A1* | 4/2009 | Goldhaber et al. ............ 705/2 |
| 2009/0149719 A1* | 6/2009 | Wariar et al. ................. 600/300 |
| 2009/0163969 A1 | 6/2009 | Donofrio |
| 2009/0192394 A1* | 7/2009 | Guttag et al. ................. 600/509 |
| 2009/0204642 A1* | 8/2009 | Gliklich ...................... 707/104.1 |
| 2009/0227883 A1* | 9/2009 | Zhang et al. ................. 600/509 |
| 2009/0299767 A1* | 12/2009 | Michon et al. ................ 705/3 |
| 2009/0326356 A1 | 12/2009 | Kracker |
| 2010/0057490 A1* | 3/2010 | Kocis et al. .................... 705/2 |
| 2010/0079292 A1 | 4/2010 | Lynn et al. |
| 2010/0113889 A1* | 5/2010 | Ghanem ....................... 600/301 |
| 2010/0145250 A1* | 6/2010 | Bene ............................ 604/6.09 |
| 2010/0174161 A1 | 7/2010 | Lynn |
| 2011/0040713 A1* | 2/2011 | Colman et al. ................ 706/16 |

OTHER PUBLICATIONS

Qune, d., et al., "Oxygen Variability, Adherence to Oxygen Saturation Targets and Chronic Lung Disease:297," Pediatric Research: Aug. 2005—vol. 58—Issue 2—p. 405.

* cited by examiner

302

304

SYSTEM AND METHOD FOR INTEGRATING CLINICAL INFORMATION TO PROVIDE REAL-TIME ALERTS FOR IMPROVING PATIENT OUTCOMES

CROSS-REFERENCE TO RELATED APPLICATIONS

This application claims the benefit of U.S. Provisional Patent Application No. 61/165,672 filed Apr. 1, 2009 and entitled "System and Method for Integrating Clinical Information to Provide Real-Time Alerts for Improving Patient Outcomes," the entirety of which is incorporated herein by reference.

SUMMARY

The present disclosure relates to alerts for improving patient outcomes and, more particularly, the present disclosure relates to integrating clinical information to provide real-time alerts for improving patient outcomes.

Real-time patient management may use real-time clinical data and physiological measures in light of the patient's condition and past medical and surgical history to estimate the patient's clinical state. Clinical management decisions can be made based on the patient's estimated clinical state. Better clinical management decisions may be made from better estimation of the patient's clinical state and from a better understanding of the association between medical interventions and patient outcomes. Medical interventions which occur soon after a patient enters a clinical state associated with poor patient outcomes typically yield better outcomes than medical interventions made after a patient has spent a longer time in this clinical state. Consequently, a real-time clinical decision support system is desired in order to provide alerts soon after patients enter untoward or unfavorable clinical states. This real-time support system may be designed to help physicians achieve improved patient outcomes.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

A combination of information representing a patient's clinical state is provided to a monitoring system. This patient information may include both patient characteristics and patient clinical information. Patient characteristics include, for example, a patient's medical history, surgical history, demographic information (e.g., age, sex, weight, body mass index (BMI), etc.). Patient clinical information includes, for example, information that can be measured from a patient (e.g., heart rate (HR), respiratory rate, blood pressure (BP—Mean Arterial Pressure (MAP), Systolic Pressure, Diastolic Pressure), as well as derived hemodynamic parameters (ratios, product or differences of heart rate and the components of BP e.g., Systolic/Diastolic or MAP/HR), Bispectral Index® (BIS®), SpO2, temperature, ScO2, etc.) and information about patient interventions (e.g., the start of a surgical procedure, intubation of the patient, the administration of drugs, etc.). The patient information may be combined by the monitoring system in order to provide a risk assessment that may guide the decision making of a physician. The updated patient information may be provided to the monitoring system in real-time which may allow the risk-assessment to be provided to the physician in real-time.

The real-time delivery of a risk assessment may allow a physician to make decisions sooner and better with more information. The monitoring system may provide alarms to alert the physician to a patient entering an undesirable state at any given moment. The alarms may further alert the physician that this undesirable state is associated with a particular outcome. For example, the alarm may indicate that the patient is going into a low BIS value state and that this state is associated with increased mortality. The physician may then provide an intervention for the patient to help place the patient in a more desirable state.

Figure 1:
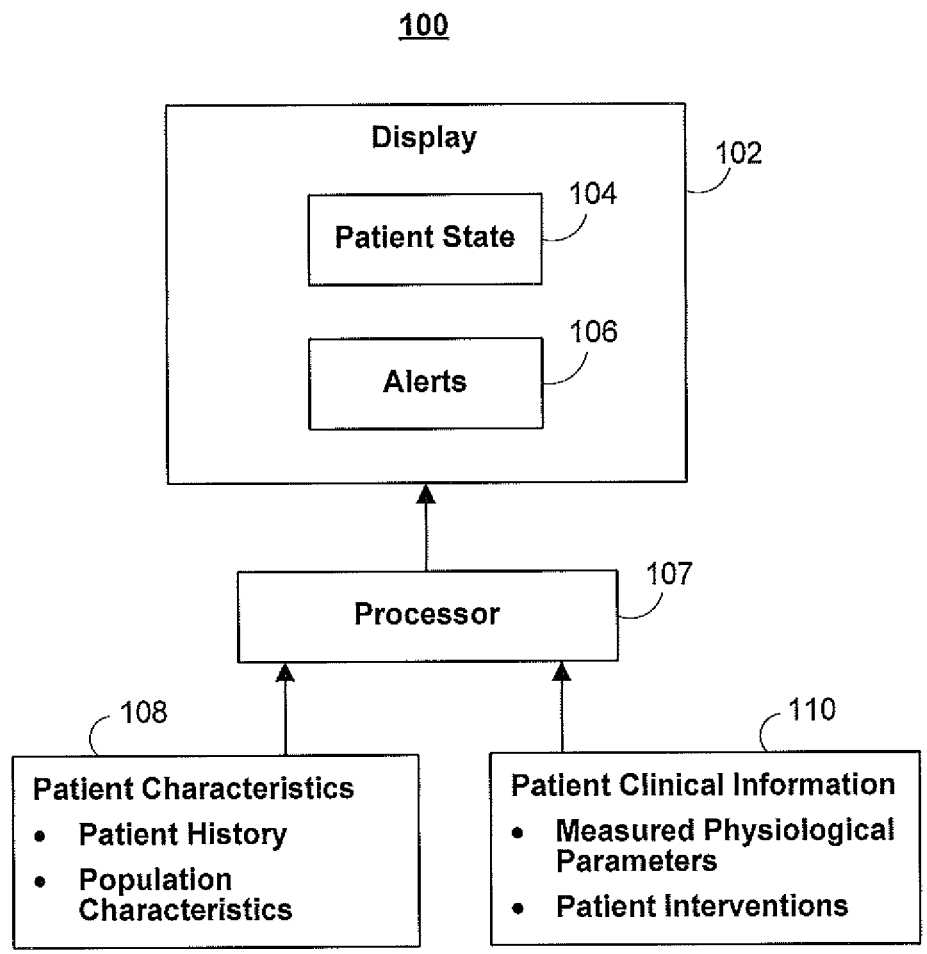
FIG. 1 is an illustrative block diagram of a patient monitoring system capable of monitoring a patient according to an embodiment.

FIG. 1 is an illustrative block diagram of a patient monitoring system 100 capable of monitoring a patient. For example, patient monitoring system 100 may be used to monitor a patient during a surgical procedure. System 100 includes a display 102 and a plurality of inputs 108 and 110. System 100 also includes processor 107 used to process inputs 108 and 110 in order to generate patient state information 104 and alerts 106. Inputs 108 and 110 may be provided from any suitable data source, data generating source, data input source, data generating equipment, or any combination thereof. For example, inputs 108 and 110 may be patient data or population data accessed from one or more memory devices (not shown) or may be data input into the system 100 using a keyboard, mouse, internet connection, automatic download or any other suitable method for inputting data known to those of skill in the art. Inputs 108 and 110 may also provide data associated with any suitable signal or signals, such as, for example, biosignals (e.g., electrocardiogram, electroencephalogram, electrogastrogram, electromyogram, heart rate signals, pathological sounds, ultrasound, plethysmogram, photoplethysmogram, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In system 100, inputs 108 and 110 may be coupled to processor 107. Processor 107 may be any suitable software, firmware, and/or hardware, and/or combinations thereof for processing inputs 108 and 110. For example, processor 107 may include one or more hardware processors (e.g., integrated circuits), one or more software modules, computer-readable media such as memory, firmware, or any combination thereof. Processor 107 may, for example, be a computer or may be one or more chips (i.e., integrated circuits). Processor 107 may perform the calculations associated with generating risk-assessment information and alerts, as well as the calculations associated with determining patient state information. Processor 107 may perform any suitable signal processing of inputs 108 and 110, such as any suitable band-pass filtering, adaptive filtering, closed-loop filtering, and/or any other suitable filtering, and/or any combination thereof.

Processor 107 of patient monitoring system 100 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by the processor to, for example, store data corresponding to patient information.

Processor 107 may be coupled to display 102. Alternatively, or in addition to display 102, processor 107 may be coupled to any suitable output device such as, for example, one or more medical devices (e.g., a medical monitor that displays various physiological parameters, a medical alarm, or any other suitable medical device that either displays physiological parameters or uses the output of processor 107 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

For ease of illustration, system 100 is shown as having two inputs, inputs 108 and 110. It will be understood that any suitable number of inputs may be used. Input 108 may receive patient characteristics including, for example, a patient's medical history, surgical history, demographic information (e.g., age, sex, weight, body mass index (BMI), etc.). Input 108 may also receive population characteristics, for example, data from a patient population database. The population characteristics may include information about a reference population. The reference population may include a data set of patient characteristics and patient clinical information for a set of patients. Input 110 may receive patient clinical information including, for example, measured physiological parameters from the patient (e.g., heart rate (HR), respiratory rate, blood pressure (BP—Mean Arterial Pressure (MAP), Systolic Pressure, Diastolic Pressure), as well as derived hemodynamic parameters (ratios, product or differences of heart rate and the components of BP e.g., Systolic/Diastolic or MAP/HR), Bispectral Index® (BIS®), SpO2, temperature, SeO2, etc.) and information about patient interventions (e.g., the start of a surgical procedure, intubation of the patient, the administration of drugs, etc.). This information may be provided to inputs 108 and 110 directly from one or more medical devices, may be accessed from one or more databases, or may be input by a user.

Figure 2:
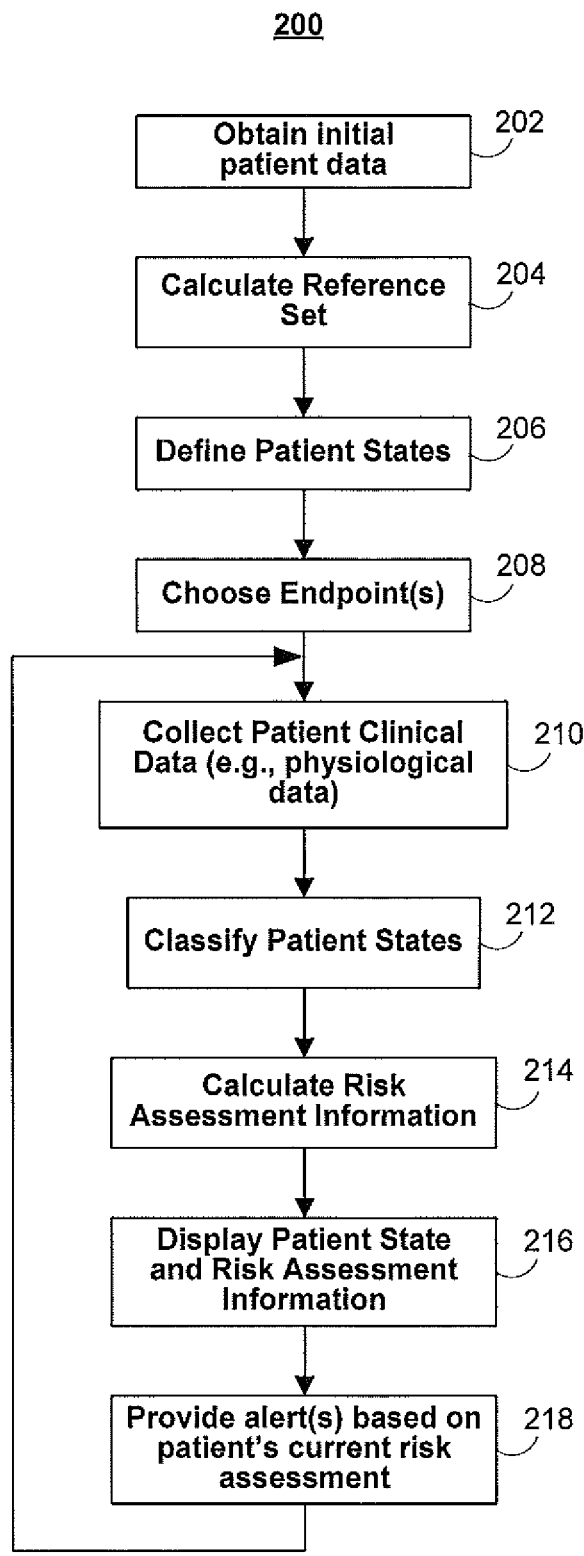
FIG. 2 is a flow chart of illustrative steps involved in calculating patient risk and providing alerts according to an embodiment.

FIG. 2 is a flow chart of illustrative steps involved in calculating patient risk and providing alerts using patient monitoring system 100 of FIG. 1 according to an embodiment. At step 202, initial patient data may be obtained, for example, using inputs 108 and 100 (FIG. 1). The initial patient data may include patient characteristics and patient clinical information. At step 204, a reference set may be calculated based on the initial patient data obtained at step 202. The reference set may also be calculated based on population characteristics, for example, data from a patient population database. These population characteristics may be stored in a memory (not shown) within patient monitoring system 100 or may be obtained using inputs 108 and 100. For example, if patient monitoring system 100 is monitoring parameters such as Bispectral Index® (BIS®), mean arterial pressure (MAP) and mean alveolar concentration (MAC), the reference set includes reference population data associated with each parameter. The calculation of reference sets and reference data will be described in greater detail with respect to the examples below. In an embodiment, one or more reference sets may be pre-calculated. These reference sets may be stored by or input to patient monitoring system 100. In this embodiment, a pre-calculated reference set may be accessed at step 204.

Any other suitable physiological parameters may be selected for monitoring by patient monitoring system 100 including, for example, other measures of hemodynamic state and cardiovascular function such as heart rate, diastolic pressure, systolic pressure, stroke volume, cardiac output and flow, and other brain monitoring measurements as well as other measures of patient brain state. Any physiological parameter that may be monitored may be considered. These physiological parameters may be the parameters that the physician is monitoring during a surgical procedure. In an embodiment, only selected physiological parameters are provided to patient monitoring system 100 to calculate patient risk. In another embodiment, multiple physiological parameters are provided to patient monitoring system 100 and only selected physiological parameters are monitored and used to calculate patient risk.

After the initial patient data is entered into patient monitoring system 100 (step 202) and a reference set has been calculated (step 204), the patient monitoring system 100 defines patient states associated with the monitored physiological parameters. The patient states define the relationship between each monitored physiological parameter of the patient and the reference set. For example, a current value of the monitored parameter in a patient may be higher than, lower than, or equal to a reference state for that parameter. In this example, higher than, lower than, and equal to the reference state are three patient states associated with the physiological parameter. In an embodiment, population-based norms may be used to define patient states. For example, a reference set for a monitored physiological parameter may be associated with a mean value or mean range of values for the parameter calculated from a patient population database. The patient state may be defined based on where the patient falls, higher than, lower than, or equal to the reference state. In an embodiment, the patient states may be adjusted from the population-based characteristics based on patient characteristics (e.g., age). The definition of patient states will be described in greater detail with respect to the examples below.

After the patient states are defined (step 206), an endpoint or a plurality of endpoints may be chosen at step 208. Endpoints are patient clinical states or patient outcomes of interest. For example, during and after a surgical procedure or hospitalization of other period of medical treatment, an endpoint may be a patient's likelihood of mortality, the length of post-operative stay of the patient, the occurrence of post surgical complications, the time to achieve an adequate level of post-operative pain, the likelihood of postoperative delirium, the likelihood of postoperative nausea and vomiting, or degree of patient satisfaction.

At step 210, patient monitoring system 100 may collect patient clinical information, for example, from inputs 108 and 110. In an embodiment, the patient clinical information may be collected in real time or substantially in real time. At step 212, patient monitoring system 100 may combine the collected patient clinical information with previously obtained patient information to classify the patient into the defined patient states. In an embodiment, patient state classifications may be determined in real time or substantially in real time.

The patient state classifications may then be used by patient monitoring system 100 to calculate risks associated with the chosen endpoints at step 214. Patient state information and risk assessment information may be displayed at step 216. Patient state information may be displayed as, for example, patient state information 104 in display 102. Patient state information may also be displayed with the determined risk assessment information. For example, patient state information 104 in display 102 may indicate that the patient is in a low BIS value state. The patient state information 104 in display 102 may also indicate that the low BIS value state is associated with an increased risk of mortality. At step 218, patient monitoring system 100 may also generate and provide one or more alerts when the patient is an undesirable patient state. The alert may be audible, visual, tactile or any other suitable alert. In some embodiments, patient monitoring system 100 may output the current patient state, the current risk assessment associated with a given endpoint, and alerts based on time spent in a particular state.

Figure 3:
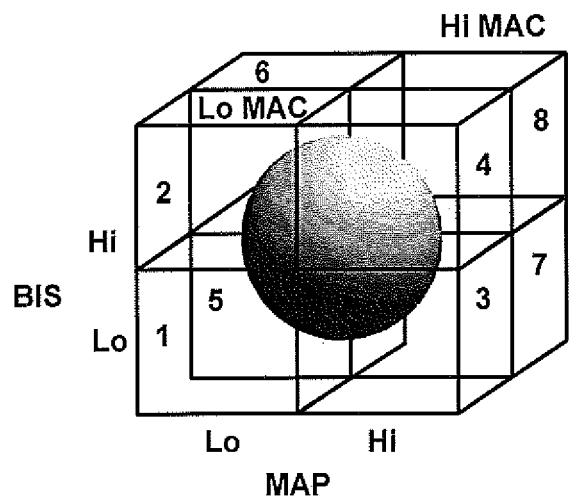
FIG. 3 shows illustrative displays of patient state and risk assessment information according to an embodiment.
Figure 3:
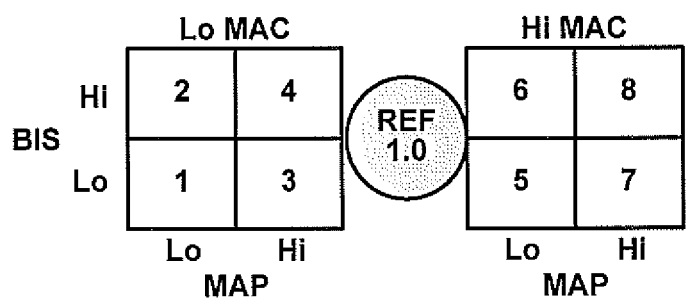

FIG. 3 shows illustrative displays of patient state and risk assessment information that may be displayed, for example, in display 102 of patient monitoring system 100 (FIG. 1). In an embodiment, the patient risk assessment information may be shown in a three-dimensional grid or space, e.g., in a 2×2×2 cube (8 cells+a central reference cell) as shown in display 302. The patient risk assessment information may also be shown in a two-dimensional grid space, where the third-dimension of plot 302 is separated into a flattened two-dimensional space (8 cells+a ninth reference cell) as shown in display 304. The reference cell in displays 302 and 304 is depicted as a sphere, however it could also be displayed as a cube, or any other suitable shape. Displays 302 and 304 will be described with reference to the following illustrative examples.

In the illustrative examples described herein, the monitoring system monitors and provides risk assessment information based on three physiological measures. The three physiological measures include, a measure of consciousness and sedation such as the Bispectral Index® (BIS®), a measure of blood pressure such as mean arterial pressure (MAP), and a measure of delivered anesthetic agent concentration such as mean alveolar concentration (MAC). It will be understood by those of skill in the art that any other suitable patient information may be used to provide risk assessment information (e.g., heart rate (HR), respiratory rate, blood pressure (BP—Mean Arterial Pressure (MAP), Systolic Pressure, Diastolic Pressure), as well as derived hemodynamic parameters (ratios, product or differences of heart rate and the components of BP e.g., Systolic/Diastolic or MAP/HR), SpO2, temperature, ScO2, etc.). Furthermore, while the illustrative patient risk assessment displays described below show patient state and risk assessment information based on these three physiological measures, it will be understood that any number of patient information variables may be used by the monitoring system to generate risk-assessment information and alerts.

The following example will illustrate the operation of patient monitoring system 100 in accordance with an embodiment. A data set of patient characteristics and patient clinical information for a set of patients may be obtained. The patient characteristics include, for example, electronic medical and surgical records for a set of patients. The patient clinical information includes, intra-operative data such as minute-by-minute measurements of: blood pressure (systolic, diastolic, MAP), heart rate, the anesthetic agent concentrations being used (delivered or expired), and other drugs that were given (e.g., muscle relaxants, analgesics, etc.).

The data set may be used to develop a set of rules to evaluate various patient risks and outcomes. The present embodiment monitors physiological parameters MAP, BIS, and MAC as measures of patient clinical state. Other embodiments may derive patient states and risk assessment information using other physiological parameters, including: other measures of hemodynamic state and cardiovascular function (e.g., heart rate, diastolic pressure, systolic pressure, SpO2, stoke volume, cardiac output and flow), other brain monitoring measurements, as well as other measures of patient brain state.

Figure 4:
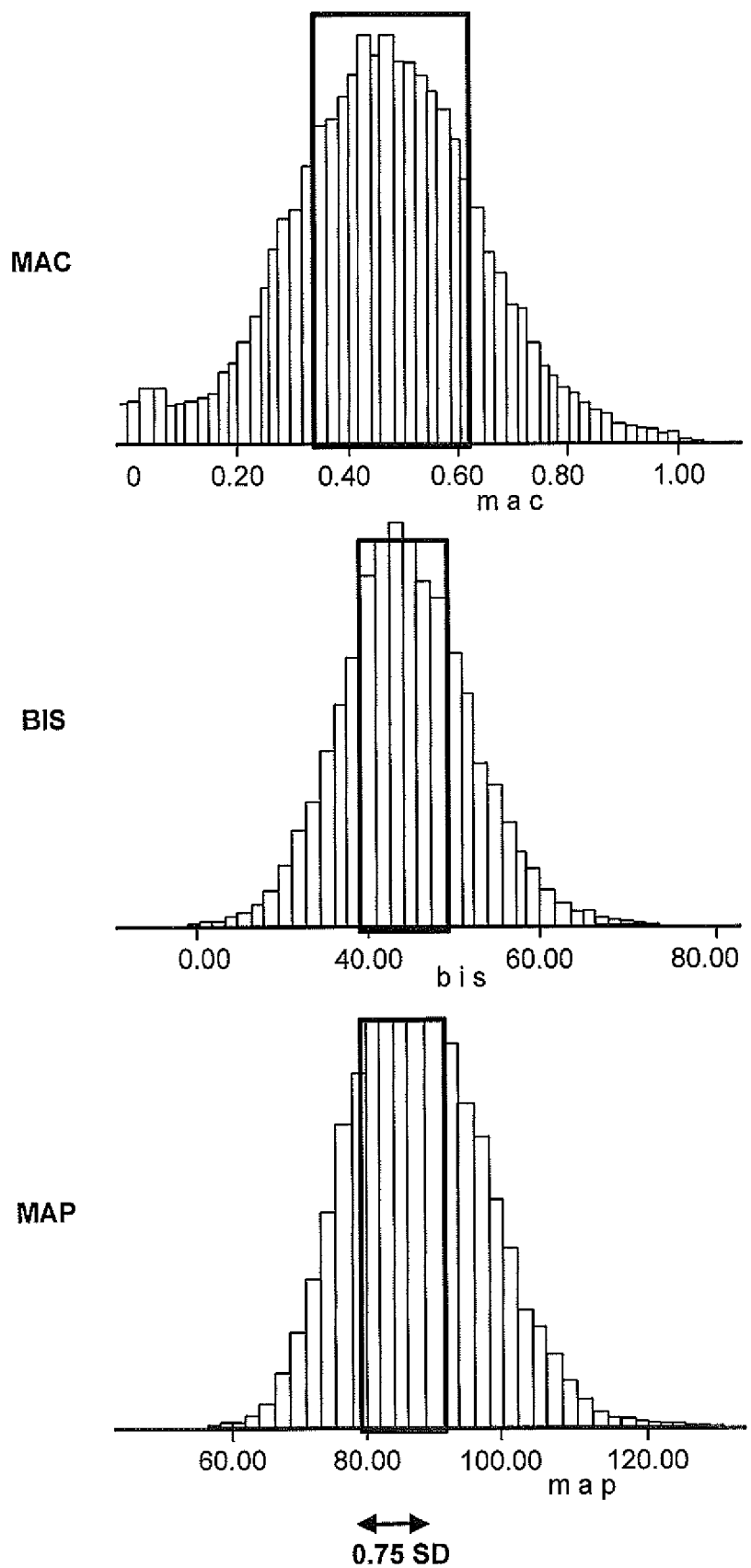
FIG. 4 shows illustrative histogram plots for population averages according to an embodiment.

The data set may be evaluated by calculating for each patient, and from the start of the case to the end of the case, the average MAC value, the average BIS value, and the average MAP value. FIG. 4 shows illustrative histogram plots of population averages for MAC, BIS, and MAP values. After all cases are plotted on the histogram, a mean for the population can be established. The cases that are within 0.75 standard deviation (SD) of the mean for all of average MAC, average BIS and average MAP may be considered typical cases and these cases may be used to define a reference population. The reference population may be expected to be about 20% of the entire population. The values of the physiological parameters for the reference population may be used to define a reference set for these parameters. In some embodiments, reference sets may be calculated at step 204 (FIG. 2) using patient monitoring system 100 (FIG. 1). In some embodiment, reference sets may be pre-determined and may be input to patient monitoring system 100 (FIG. 1).

In addition to the reference state, eight additional patient states may be defined by being outside of the reference state and being either higher or lower than the population mean of MAP, MAC and BIS. As illustrated in Table 1, patient states may be defined based on the sections of the population that do not fall within the reference group, as either being high or low relative to the reference population, thus creating eight cells. These eight cells may also be represented as part of a three-dimensional cube (FIG. 3, display 302) or two-dimensional squares (FIG. 3, 304). The patient state may be defined by where the patient falls, either higher or lower than the reference population for each of the evaluated parameter. In addition to these eight patient states, a ninth patient state may be defined in which the patient falls within the reference population for all of the evaluated parameters. The reference state may be the condition when the patient is within 0.75 standard deviation of the mean of each parameter (e.g., BIS, MAP and MAC). In certain embodiments, if any of the BIS, MAP and MAC are outside 0.75 SD away from their respective mean, then they are in one of the 8 other states (listed in Table 1 below).

TABLE 1

Characterization of Patient States

| | | | |
|---|---|---|---|
| Patient State 1 | Lo MAC | Lo MAP | Lo BIS |
| Patient State 2 | Lo MAC | Lo MAP | Hi BIS |
| Patient State 3 | Lo MAC | Hi MAP | Lo BIS |
| Patient State 4 | Lo MAC | Hi MAP | Hi BIS |
| Patient State 5 | Hi MAC | Lo MAP | Lo BIS |
| Patient State 6 | Hi MAC | Lo MAP | Hi BIS |

TABLE 1-continued

Characterization of Patient States

| Patient State 7 | Hi MAC | Hi MAP | Lo BIS |
| Patient State 8 | Hi MAC | Hi MAP | Hi BIS |

Each patient state may have one or more associated hazard ratios derived from a model. FIGS. 5-8 include illustrative two-dimensional patient risk assessment charts including associated hazard ratio parameters. These hazard ratios may be calculated using a proportional hazards model such as, for example, the Cox proportional hazards model. The Cox proportional hazards model may be used to calculate the relative risk of a given endpoint relative to the patients treated in the reference population. The hazard ratios for each of the patient states may be used to determine which of the calculated risks or hazard ratios are statistically different from that of the reference population. A hazard ratio greater than 1 may indicate an increased likelihood of the given event (i.e., endpoint) happening. A hazard ratio less than 1 may indicate a decreased likelihood of the given event (i.e., endpoint) happening.

Figure 5:
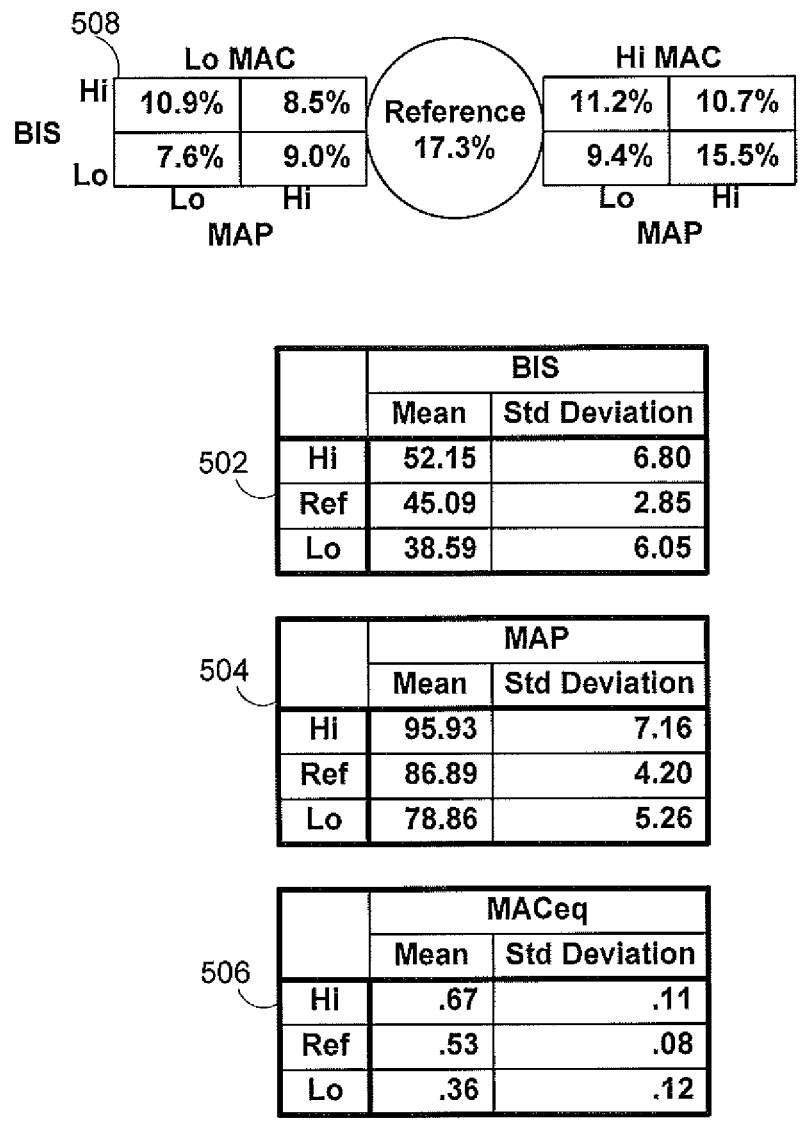
FIG. 5 shows an illustrative chart of the distribution of the population for each patient state according to an embodiment

After patient information is collected and the patient is classified into one or more patient states (e.g., at steps 210 and 212 of FIG. 2), the patient state information may be displayed in a three-dimensional or two-dimensional format. Patient state information for each of the monitored physiological parameters may be defined based on the distribution of the reference population for each state. Chart 508 of FIG. 5 is an illustrative chart that shows the proportion of patients that are in each of the defined patient states. Tables 502, 504, and 506 indicate the mean and standard deviation values for the Lo, Hi, and reference states for each of the 3 parameters (BIS, MAP, and MAC). This information may be displayed, for example, on display 102 of patient monitoring system 100. The current patient state for a patient may be visually distinguished (e.g., highlighted) to indicate the patient state to a physician.

After patient state information is determined (and displayed), the risk associated with the chosen endpoint(s) may be calculated (and displayed). In the example illustrated in FIG. 6, the endpoint chosen is patient mortality rate. Patient state information may be analyzed to determine the relative risk of death for a patient, relative to the reference population, within various time periods after a particular procedure: in-hospital, 30-days, 90 days and 1-yr. The reference population incidence of mortality, in this example, for in-hospital is 0.5%, for 30 days: 0.9%, for 90 days: 1.9% and for 1 year: 4.1%. A Cox proportional hazards model may be used to derive the relative risk of mortality at each of the mortality time points using the average BIS, average MAC, and average MAP, along with patient demographic and comorbidity measures. The relative risk (hazard ratio) of each mortality endpoint is calculated for each patient state and displayed within associated patient state cells in FIG. 6. The current patient state for a patient may be visually distinguished (e.g., highlighted) to indicate the patient state to a physician.

Figure 6:
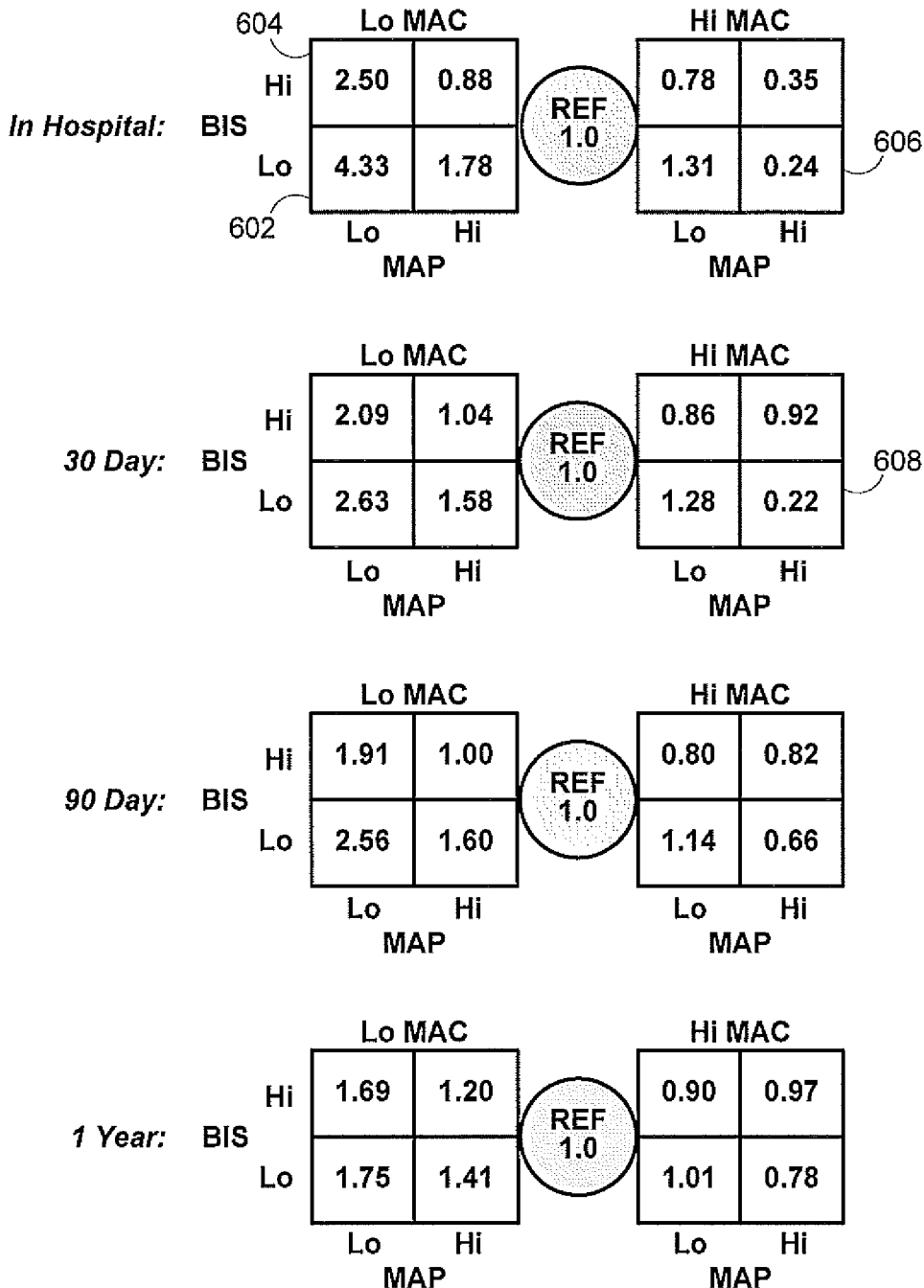
FIG. 6 shows an illustrative chart of the relative risk hazards for each patient state based on a mortality endpoint according to an embodiment.

After the hazard ratios are calculated, the ratios may be analyzed to determine if the relative risk of mortality at each of the patient states is significantly statistically different from the reference population (p<0.05). In the example illustrated in FIG. 6, patient states 602 and 604 are undesirable patient states in terms of mortality, as indicated by the relatively high hazard ratio of 4.43 and 2.50, respectively. The patients whose measured BIS, MAP and MAC values place them in these states may have a higher risk of mortality than those whose measured BIS, MAP and MAC values place them in the reference population. On the other hand, patient states 606 and 608 may be associated with a lower risk of mortality relative to the reference group. In this manner, these hazard ratios may indicate which of the patient states are desirable or undesirable relative to the chosen endpoint(s). This information may be used in a patient monitor, e.g., patient monitoring system 100, to continuously calculate patient state information and to display risk assessment information. For example, the patient monitor may be configured to alert a physician if the patient transitions into or is in one of the undesirable (high-risk) states for more than a predetermined period of time. In the example of FIG. 6, the undesirable states are patient states 602 and 604. The physician may then intervene to adjust the patient's parameters and drive the patient into a more desirable state.

Figure 7:
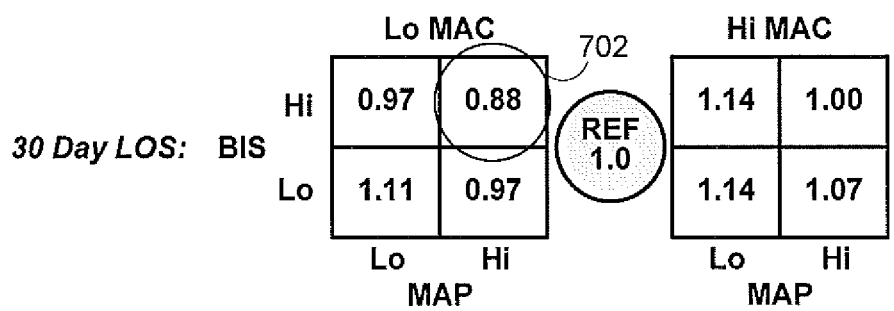
FIG. 7 shows an illustrative chart of the relative risk hazards for each patient state based on a length of stay endpoint according to an embodiment.

FIG. 7 shows an illustrative example of calculated relative risk hazards associated with a length of stay (LOS) endpoint and a mortality endpoint. Here, hazard ratios may be calculated for patients based on time to discharge from the hospital within 30 days of admission (30 day length of stay). The one year mortality rate for the 30-day LOS patients may also be analyzed. In this example, patient state 702 is associated with the most desirable outcome in terms of LOS (i.e., the shortest time to discharge), as shown by the relatively low hazard ratio of 0.88.

Figure 8:
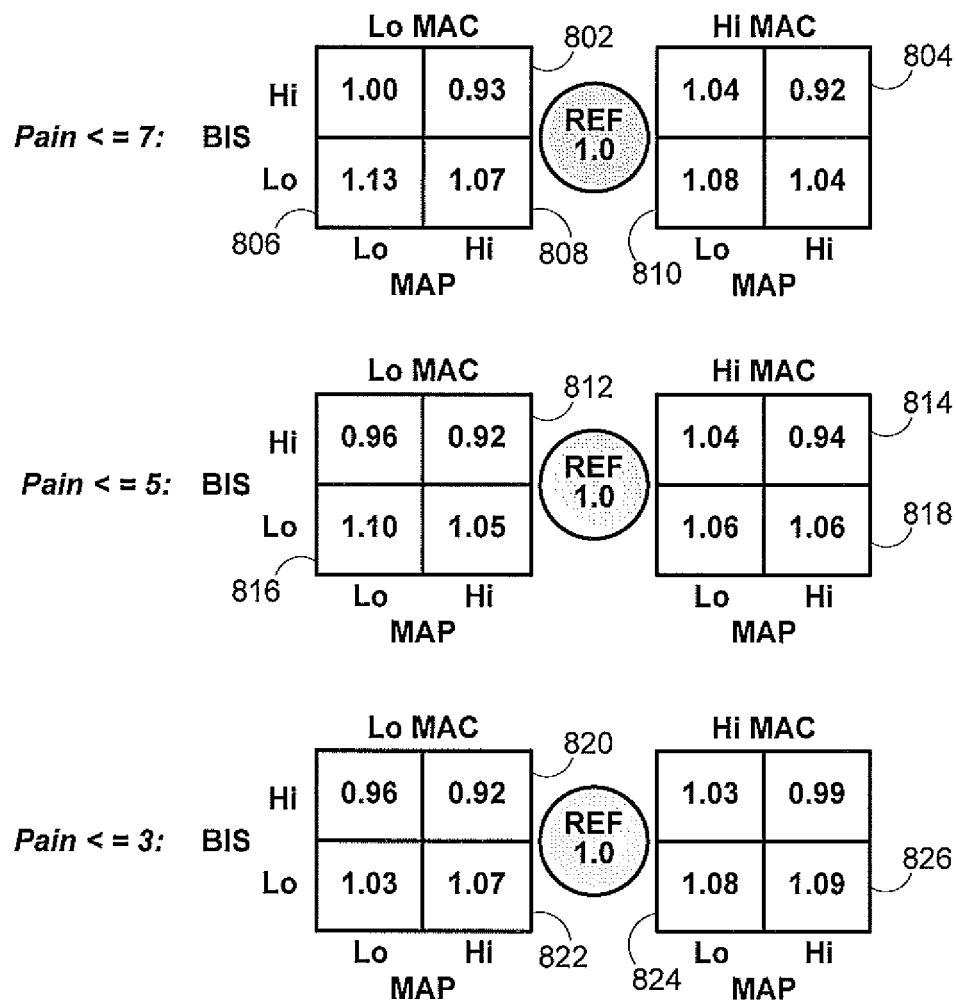
FIG. 8 shows an illustrative chart of the relative risk hazards for each patient state based on a level of pain endpoint according to an embodiment.

FIG. 8 shows an illustrative example of calculated relative risk hazards associated with time until relief of post-op pain. Relative risk for the patient to be at a certain pain level within 192 hours may be calculated for each of the patient states. The pain level is on a scale of 1 to 10, with 10 being the highest level of pain. From the hazard ratios, for a patient to reach a pain level of 7 within the 192 hours, patient states 802 and 804 are associated with a faster recovery time while patient states 806, 808, 810 are associated with a slower recovery time. For a pain level of 5 within 192 hours, patient states 812 and 814 are associated faster recovery time, while patient states 816 and 818 are associated with a slower recovery time. For a pain level of 3 within 192 hours, patient state 820 is associated with a faster recovery time while patient states 822, 824, and 826 are associated with a slower recovery time.

The following are additional illustrative examples in which clinical data and physiological measures may be used to estimate a patient's clinical state in accordance with an embodiment. A duration of the "triple low" (i.e., low MAP, low MAC, and low BIS value states) may be associated with various outcomes, including: complications, post-operative pain, length of stay, readmission, and 30-day and 1-year mortality. In one example, increasing duration of the triple low may be associated with worsened postoperative recovery (pain, complications, excess LOS), 30-day readmission, and postoperative mortality (30-day and 1-year). Early recognition of the triple low may allow adjustments in anesthetic or medical management that could improve patient outcomes. According to another example, the risk of one year postoperative mortality may be higher among patients who did not receive vasopressor administration while in a triple low state. Thus, vasopressor administration soon after patients enter the triple low state may improve the risk of mortality, as compared to later vasopressor administration. According to yet another example, the combination of low MAC and low MAP values may be a strong and highly statistically significant predictor for mortality. When combined with a low BIS value, mortality may be even greater. The combination of low MAC, low MAP, and low BIS (i.e., a triple low) may be associated with a nearly tripled risk of mortality at 30 days, and nearly doubled risk of mortality at one year.

The foregoing is merely illustrative of the principles of this disclosure and various modifications can be made by those skilled in the art without departing from the scope and spirit of the disclosure.

What is claimed is:

1. A system for monitoring a patient during a clinical visit comprising:
   an input for receiving input data;
   a sensor configured to collect physiological data of a patient;
   a display; and
   a processor configured to:
   receive, from the input, one or more patient characteristics,
   determine a reference population data set based on the one or more patient characteristics,
   define a plurality of patient states from the reference population data set,
   receive, from the sensor, physiological data of the patient,
   classify the patient as being in one of the plurality of patient states based on a comparison between the collected physiological data and the reference population data set, wherein each of the patient states is associated with a risk of a particular health outcome,
   provide, using the display, the risk associated with the patient state classification,
   receive, from the input, data identifying a clinical intervention performed on the patient,
   receive, from the sensor, updated physiological data of the patient,
   update the patient state classification based on the data identifying the clinical intervention and the updated physiological data, and
   provide, using the display, the risk associated with the updated patient state classification.

2. The system of claim 1, wherein the one or more patient characteristics comprise at least one of the patient's medical history and demographic information.

3. The system of claim 2, wherein the physiological data comprises real-time physiological parameters of the patient.

4. The system of claim 3, wherein the real-time physiological parameters are selected from the group consisting of heart rate, respiratory rate, blood pressure, derived hemodynamic parameters, measure of consciousness, SpO2, temperature and ScO2.

5. The system of claim 4, wherein the patient state classification is further based on the real-time physiological parameters and input data comprising a medical history of the patient.

6. The system of claim 4, wherein the risks associated with the plurality of patient states are based on a reference population data set.

7. The system of claim 1, wherein the system further comprises an alarm capable of notifying a physician when the patient is in an undesirable patient state.

8. The system of claim 1, wherein the display displays information in a 3-dimensional format.

9. The system of claim 1, wherein the display displays information in a 2-dimensional format.

10. A method for monitoring a patient during a clinical visit, the method comprising:
    receiving, from an input, one or more patient characteristics;
    determining a reference population data set based on the one or more patient characteristics;
    defining a plurality of patient states from the reference population data set;
    receiving, from a sensor, physiological data of a patient;
    with a processor, classifying the patient as being in one of the plurality of patient states based on a comparison between the received physiological data and the reference population data set, wherein each of the patient states is associated with a risk of a particular health outcome;
    displaying, on a display device, the risk associated with the patient state classification;
    receiving data identifying a clinical intervention performed on the patient;
    receiving, from the sensor, updated physiological data from the patient;
    updating the patient state classification based on the data identifying the clinical intervention and the updated physiological data; and
    displaying, on the display device, the risk associated with the updated patient state classification.

11. The method of claim 10 further comprising:
    identifying a particular health outcome; and
    calculating the risk of the particular health outcome associated with each of the plurality of patient states.

12. The method in claim 11 wherein risks are calculated based at least in part on a Cox Regression model.

13. The method of claim 10, wherein the one or more patient characteristics comprise at least one of the patient's medical history and demographic information.

14. The method of claim 13, wherein the physiological data comprises real-time physiological parameters of the patient.

15. The method of claim 14, wherein the real-time physiological parameters are selected from the group consisting of heart rate, respiratory rate, blood pressure, derived hemodynamic parameters, measure of consciousness, SpO2, temperature and ScO2.

16. The method of claim 15, wherein the patient state classification is further based on the real-time physiological parameters and input data comprising a medical history of the patient.

17. The method of claim 11, wherein an alert is provided when the patient is in an undesirable patient state.

18. The method of claim 17, wherein the alert is provided each time a patient is in an undesirable patient state for a time duration exceeding a threshold duration.

19. The method of claim 10, wherein the risk assessment is displayed in a 3-dimensional format.

20. The method of claim 10, wherein the risk assessment is displayed in a 2-dimensional format.

21. The method of claim 11, wherein the plurality of patient states are defined based at least in part on measure of consciousness, mean arterial pressure (MAP), and mean alveolar concentration (MAC).

22. The method of claim 21, wherein the plurality of patient states are defined based at least in part on SpO2, temperature and ScO2.

23. The method of claim 11, wherein the plurality of patient states are defined based at least in part on at least two or more of measure of consciousness, mean arterial pressure (MAP), mean alveolar concentration (MAC), MAP/Heart Rate (HR), SpO2 and ScO2.

* * * * *